(12) United States Patent
Wiese et al.

(10) Patent No.: US 7,381,838 B2
(45) Date of Patent: Jun. 3, 2008

(54) PREPARATION OF TERTIARY CARBOXYLIC ACIDS

(75) Inventors: Klaus-Diether Wiese, Haltern am See (DE); Wilfried Bueschken, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 162 days.

(21) Appl. No.: 11/071,166

(22) Filed: Mar. 4, 2005

(65) Prior Publication Data

US 2005/0197507 A1   Sep. 8, 2005

(30) Foreign Application Priority Data

Mar. 6, 2004  (DE)  ................ 10 2004 011 081

(51) Int. Cl.
  *C07C 51/14* (2006.01)
  *C07C 51/10* (2006.01)
(52) U.S. Cl. ...................... 562/521; 562/517
(58) Field of Classification Search ........... 562/512, 562/517, 521, 522, 606
See application file for complete search history.

(56) References Cited

U.S. PATENT DOCUMENTS

| | | | |
|---|---|---|---|
| 5,646,332 A * | 7/1997 | Cusumano et al. | 560/204 |
| 5,981,796 A * | 11/1999 | Breed et al. | 562/521 |
| 6,340,778 B1 | 1/2002 | Bueschken et al. | |
| 6,492,564 B1 * | 12/2002 | Wiese et al. | 568/451 |
| 6,500,979 B1 | 12/2002 | Wiese et al. | |
| 6,555,716 B2 | 4/2003 | Protzmann et al. | |
| 6,603,047 B2 | 8/2003 | Wiese et al. | |

FOREIGN PATENT DOCUMENTS

| | | |
|---|---|---|
| EP | 1 057 525 A2 | 12/2000 |
| EP | 1 106 594 A2 | 6/2001 |
| EP | 1 106 596 A2 | 6/2001 |

OTHER PUBLICATIONS

Perry's Chemical Engineers' Handbook (7th Edition) Edited by: Perry, R.H., Green, D.W. © 1997 McGraw-Hill, pp. 23:49-50.*
Yoshie Souma, et al., "Carbonylation of Alcohols, Olefins, and Saturated Hydrocarbons by CO in the Ag(I)-$H_2SO_4$ System", Bulletin of the Chemical Society of Japan, vol. 47, No. 7, Jul. 1974, pp. 1717-1719.
"Koch Reactions", New Synthesis with Carbon Monoxide, J. Falbe (Ed), Springer, Berlin, 1980, pp. 372-413.

* cited by examiner

*Primary Examiner*—Karl Puttlitz
(74) *Attorney, Agent, or Firm*—Oblon, Spivak, McClelland, Maier & Neustadt, P.C.

(57) ABSTRACT

Process for carrying out catalytic multiphase reactions in a tubular reactor, in which at least three reactants are present in three different phases, wherein the process is carried out in at least one tubular reactor, and the catalyst is present in a continuous phase, at least one reactant is present in this continuous phase, and at least two reactants are present dispersed in the continuous phase and the loading factor B of the tubular reactor is equal to or greater than 0.2. In particular, the multiphase reaction is a hydrocarboxylation of at least one olefin to a carboxylic acid.

16 Claims, 1 Drawing Sheet

PREPARATION OF TERTIARY CARBOXYLIC ACIDS

BACKGROUND OF THE INVENTION

1. Field of the Invention

The present invention relates to a process for carrying out a multiphase reaction in which at least three reactants are involved, a process for preparing carboxylic acids by hydrocarboxylating olefins, products obtained by the multiphase reaction process, and uses thereof.

2. Description of the Related Art

Tertiary carboxylic acids may be used for the preparation of siccatives, peroxides and lubricants. A further field of use of tertiary carboxylic acids is the preparation of unsaturated esters such as vinyl esters, from which co-oligomers or copolymers are prepared.

Since the 1960s, the direct carbonylation of olefins with carbon monoxide to give carboxylic acids using strong acids as a catalyst (Koch reactions, in New Synthesis with Carbon Monoxide, J. Falbe (Ed.), Springer, Berlin, 1980, p. 372) has been known. Later, it was found that the reaction can additionally be catalyzed by silver or copper cations (Y. Souma, H. Sano, Bull. Chem. Soc. Jpn. 1974, 47, 1717). These reactions, irrespective of the starting olefin, form predominantly tertiary carboxylic acids when the starting olefin has a sufficiently large number of carbon atoms (e.g., n in the formula specified below is greater than 3):

$C_nH_{2n}+CO+H_2O \rightarrow R^1R^2R^3C-COOH$ where $(R_1+R^2+R^3)=C_{n-1}H_{2n+1}$ catalyst Industrially, these reactions are typically carried out in stirred reactors at from 40 to 70° C. and from 70 to 100 bar of CO pressure using a $BF_3/H_2O$ or $BF_3/H_3PO_4/H_2O$ catalyst. The use of catalysts having Cu ions allows the reaction to be carried out even at ambient temperature and standard pressure.

Disadvantages in all known processes include the oligomerization of a portion of the olefins to form oligomers which may partly convert to higher carboxylic acids. A further disadvantage is a low mass transfer between the phases thus resulting in low space-time yields.

SUMMARY OF THE INVENTION

It is therefore an object of the present invention to provide a process which does not have at least one of the disadvantages mentioned.

From an industrial point of view, the known processes for preparing carboxylic acids are multiphase reactions. Multiphase reactions refer to reactions which proceed with involvement of two or more immiscible or only partly miscible fluid phases. This relates, for example, to reactions between a gas phase and a liquid phase (gl), between two liquid phases which are immiscible or have a miscibility gap (ll) and reactions in which either two liquid, immiscible or only partly miscible phases and also a gas phase are involved (gll).

Examples of industrially important gas-liquid reactions (gl) include the hydroformylation of liquid olefins using a catalyst dissolved in organic phase, the reaction of acetylene with carboxylic acids and hydrogenations with homogeneously dissolved catalysts or oxidations with air or oxygen.

Applicants have recognized that a problem common to the known reactions is mass transfer since the reactants are present in different phases. Applicants have further recognized that multiphase reactions are associated with a series of further problems which makes the use of multiphase reactions in providing their industrial performance substantially more difficult than in the case of simple homogeneous reactions. Some typical problems are mentioned hereinbelow:

In known cases the substances have to be intimately contacted with one another in order to minimize the problem of mass transfer: a very large mass transfer surface $a_s$ has to be generated. On the other hand, it has to be possible to separate the phases again on completion of reaction: excessive mixing may lead to problems. The presence of two liquid phases may lead to emulsion formation, and gas-liquid processes to foaming. In a 3-phase process all problems may occur simultaneously.

In addition to a high mass transfer surface $a_S$, a very high mass transfer coefficient $k_1$ should be achieved in all multiphase reactions. Overall, the KLA value should be maximized, i.e. the product of $k_1$ and $a_S$ in the mass transfer equation

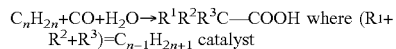

where $j$ [mol/s] is the molar flow rate of the reacting component passing through the phase interface, $k_1$ [m/s] is the mass transfer coefficient, $a_S$ [m²] is the phase interface in the reactor, $C^*$ [mol/m³] is the maximum solubility of the reactant in the second phase and $C$ [mol/m³] is the actual concentration of the reactant which is in turn coupled to the reaction rate.

Applicants have recognized that a further problem in multiphase reactions is heat removal from exothermic reactions. If the reaction rate is successfully increased by improving the mass transfer more heat has to be removed, which can lead to an undesired temperature increase right up to runaway of the reaction.

One solution for these problems of the multiphase reaction includes the use of a stirred tank reactor. However, the use of a stirred tank may lead to backmixing, which lowers the effective concentration of the reactants and leads to a decrease in the space-time yield. This disadvantage has to be paid for by the capital cost of expensive reaction space.

In the case of the Koch reaction (i.e., the reaction of olefins with CO and water to give carboxylic acids) in a 3-phase system, the process control is particularly difficult since the reactants are present in three separate phases. Both the olefins and synthesis gas have to be transported into the aqueous catalyst phase in order to come into contact with the catalyst there. Finally, there has to be transport back out of the aqueous phase. Since the transport operations are frequently slower than the actual reaction, such reactions are determined by the rate of mass transfer, and this is referred to as a transport-limited reaction.

Applicants have recognized that a need exists for a process for carrying out multiphase reactions which avoids the aforementioned disadvantages and additionally can be realized industrially in a simple manner.

It is thus also an object of the present invention to provide a process for carrying out multiphase reactions which is particularly suitable for the preparation of (tertiary) carboxylic acids by hydrocarboxylation (Koch reaction) of olefins.

DETAILED DESCRIPTION OF THE INVENTION

Figure 1:
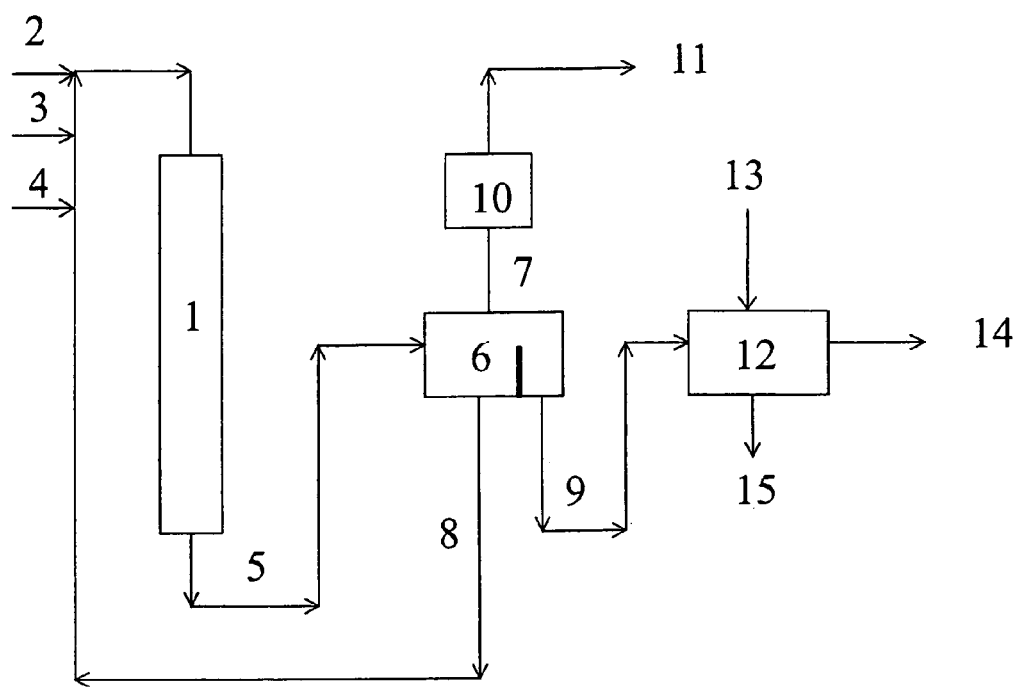
FIG. 1 shows a block diagram of a plant using an embodiment of the invention process.

Industrially, a process should fulfill one or more, or substantially all requirements for a multiphase process:
- generation of a high and stable mass transfer between the phases involved
- simple to perform, if possible with customary technical apparatus
- simple and safe heat removal
- high operational safety
- simple and safe scale-up With regard to the preparation of tertiary carboxylic acids to be carried out, special additional requirements may include one or more of the following:
- high selectivity, avoidance especially of high-boiling by-products
- only minor catalyst discharge, if any
- high space-time yields, small reactors
- high product purity Processes for carrying out multiphase reactions in which two reactants are present in different phases are known for some reactions. For instance, U.S. Pat. No. 6,500,979 describes the reaction of acetylene with carboxylic acids to give vinyl esters, U.S. Pat. No. 6,492,564 and U.S. Pat. No. 6,555,716 the hydroformylation of olefins to give aldehydes, U.S. Pat. No. 6,340,778 the preparation of unsaturated aldehydes by aldol condensation of aldehydes and U.S. Pat. No. 6,603,047 the preparation of unsaturated ketones by aldol condensation of aldehydes with ketones (each of which are incorporated herein by reference in their entirety).

It is common to all of these processes that the reaction is carried out continuously in a tubular reactor in which there is a continuous catalyst phase in which the reactants are dispersed, and that a minimum loading factor B is observed.

It has now been found that, surprisingly, carrying out a multiphase reaction in a tubular reactor while observing a minimum loading factor B is also suitable for carrying out multiphase reactions in which at least three reactants are present in different phases. In particular, it has been found that, surprisingly, olefins can be reacted with water and carbon monoxide in a tubular reactor while observing the minimum loading factor with high space-time yields and/or with high selectivities to give carboxylic acids. This is especially surprising because one reactant, i.e. the water, in this reaction is dissolved homogeneously in the catalyst phase, while the starting olefin is present in a liquid organic phase and the carbon monoxide in the gas phase.

In one embodiment the present invention provides a process for carrying out multiphase reactions in which at least three reactants are present in three different phases in a tubular reactor, wherein the process is carried out in at least one tubular reactor, and the catalyst is present in a continuous phase, at least one reactant is present in this continuous phase, and at least two reactants are present dispersed in the continuous phase and the loading factor B of the tubular reactor is greater than or equal to 0.2. In another embodiment, the invention provides a process for catalytically preparing carboxylic acids by multiphase reaction of at least one olefin with water and carbon monoxide in the presence of a catalyst in a tubular reactor which has a loading factor B of $\geq 0.2$.

In one embodiment the invention process has the advantage that the preparation of carboxylic acids succeeds with high space-time yields. The high space-time yields allow relatively small reactors to be used, which leads to a distinctly more economically viable procedure. Likewise advantageous are the relatively high selectivity, in particular the avoidance of high-boiling by-products. The low by-product formation allows carboxylic acids having a high product purity to be prepared.

Another embodiment of the invention process may be used for carrying out multiphase reactions in which at least three reactants are present in three different phases in a tubular reactor described hereinbelow, without the invention being restricted to this embodiment.

The inventive catalytic multiphase reaction process includes an embodiment in which at least three reactants are present in three different phases. The reaction is carried out in at least one tubular reactor, and the catalyst is present in a continuous phase, at least one reactant is present homogeneously throughout this continuous phase, and at least two reactants are dispersed in the continuous phase in the form of, for example, micelles, and the loading factor B of the tubular reactor is greater than or equal to 0.2. In an embodiment the invention may relate to a process for catalytically preparing carboxylic acids by multiphase reaction of at least one olefin with water and carbon monoxide in the presence of a catalyst in a tubular reactor, the catalyst being present in the continuous phase in which the starting olefin and carbon monoxide are dispersed, and the loading factor of the reactor is greater than or equal to 0.2.

The tubular reactor may contain random packings or internals. Random packings in the context of the present invention include, for example: Raschig rings, saddles, Pall rings, Tellerettes, wire mesh rings, wire mesh fabrics. Examples of internals are filter plates, baffles, column trays, perforated sheets or other mixing apparatus or combinations thereof. However, also conceivable as internals in the context of the present invention are a plurality of narrow tubes connected in parallel, thus resulting a multitube reactor. Structured mixer packings or demister packings may give enhanced performance.

In one embodiment the process includes the observance or exceedance of a minimal cross-sectional loading of the tubular reactor. In the case of upward operation of the reactor (flow direction from bottom to top), the flood point should be exceeded. The reactor may thus be operated above the point at which bubble columns are typically operated. In the case of downward operation (flow direction from top to bottom), the cross-sectional loading may be adjusted in such a way that the reactor is fully flooded or substantially flooded. Operation may thus be effected above the point which can still be referred to as a trickle bed.

For a more precise definition of the minimum reactor loading, the loading factor B of the tubular reactor may be calculated as a dimensionless pressure drop with $$B=PD/PS$$

where PD [Pa/m] is a length-based pressure drop over the reactor under operating conditions and PS [Pa/m] is an arithmetic parameter having the dimension of a length-based pressure, defined as the ratio of mass flow rate M [kg/s] of all components in the reactor to the volume flow rate V [m$^3$/s] of all components under operating conditions, multiplied by g=9.81 m/s$^2$, i.e. PS=(M/V)*g.

For illustration purposes, PS may be the static pressure per meter of a multiphasic mixture in a vertical tube if all phases were to flow at the same rate. PS is purely an arithmetic parameter which arises from the mass flow rates fed to the reactor and which can be specified irrespective of the flow direction of the reactor, the flow rate of all phases or the flooding state of the reactor.

The pressure drop PD [Pa/m] is used as an arithmetic parameter in order to determine the process conditions and can be calculated by common methods for mono- or multiphase flows. Common methods for calculating the pressure drop PD in tubes, internals or random packings, etc. may be found in, for example, the VDI-Wärmeatlas [VDI heat atlas], 7th extended edition, VDI-Verlag GmbH, Dusseldorf 1994, sections La1 to Lgb7, and also in the reference work Heinz Brauer, Grundlagen der Einphasen- und Mehrphasenströmungen [Fundamental principles of monophase and multiphase flows], Verlag Sauerländer, Aarau and Frankfurt am Main, 1971, (further editions Brauer et al.) (those sections of each of which are relevant to pressure drop calculations are incorporated herein by reference).

The pressure drop PD in the case of monophasic flow through an empty pipe is given by $$PD = Cw * \rho/2 * w^2/D$$

where $\rho$ [kg/m$^3$] density of the flowing medium under operating conditions, w [m/s] flow rate (volume flow rate/cross-sectional area), D [m] pipe diameter and Cw [–] resistance coefficient of the pipe flowed through.

In the case of flow through random packings, beds or internals, the flow rate w is to be replaced by the effective flow rate $(w/\psi)$, and the pipe diameter D by the hydraulic channel diameter $d_H$ of the random packings or internals, so that:

$$PD = Cw * \rho/2 * (w/\psi)^2 * 1/d_H$$

where $d_H$ [m] is the hydraulic channel diameter $\psi$ [–] is the empty pipe fraction Cw [–] is the resistance coefficient of the packed apparatus flowed through.

The packing-specific data $d_H$ and $\psi$ are frequently part of the delivery specifications of random packings. For a series of random packings, data are reported in the abovementioned VDI-Wärmeatlas.

The empty pipe fraction $\psi$ may also be determined experimentally by, for example, determining the capacity of the reactor before and after charging with the random packings. The hydraulic channel diameter may in turn, if not known, be calculated from the specific surface area F [m$^2$/m$^3$] of the random packings or internals (generally known or determinable experimentally) by the simple relationship $$d_H = 4\psi/F.$$

The resistance coefficient of tubes, internals and random packings is generally described as a function of the Reynolds number Re which gives information about the flow state under the selected conditions. In the case of random packings, internals, etc., the following relationship can almost always be applied:

$$Cw = K_1/Re^n + K_2/Re^m$$

where, frequently, n=1, m=0 (approach of S. Ergun, Chem. Engng. Progr. 48, (1948), 89, incorporated herein by reference), or n=1, m=0.1 (approach of Brauer et al., incorporated herein by reference). $K_1$, $K_2$ are packing-specific constants which are disclosed by delivery data or by the literature (examples can be found in VDI Wärmeatlas and in Brauer et al.). However, they may also be determined experimentally by operating the tubular reactor having random packings with a liquid under different flow rates and calculating the pressure drop Cw measured as a function of Re from the known data.

The dimensionless Reynolds number Re, finally, is defined as

Re=w*($\rho/\eta$)*D for empty pipes or

Re=(w/$\psi$)*($\rho/\eta$)*$d_H$ for pipes having internals or random packings. $\eta$ [Pa*s] denotes in each case the viscosity and $\rho$ [kg/m$^3$] the density of the flowing medium.

The pressure drop in the case of biphasic flows (here gas-liquid for carbon monoxide/catalyst solution) increases greater than proportionally. Usually, in accordance with Lockhart-Martinelli (in Brauer et al.), the pressure drop of the biphasic flow $P_{lg}$ is based on the pressure drop of one of the two phases, for example on the pressure drop of the pure flowing liquid phase $P_l$, and placed in relation to the ratio of the pressure drop of the two as phases $P_l$ and $P_g$ considered as flowing alone.

To calculate the pressure drops in biphasic flows, dimensionless pressures according to $\phi^2 = P_{lg}/P_l$ and $X^2 = P_l/P_g$ are frequently used. A further relationship $\phi^2$=function($X^2$) has been investigated many times. Examples can be found in the following references, each of which is incorporated herein by reference:

Y. Sato, T. Hirose, F. Takahashi, M. Toda: "Pressure Loss and Liquid Hold Up in Packed Bed Reactor with Cocurrent Gas-Liquid Down Flow"; J. Chem. Chem. Eng. Of Japan, Vol 6 (No. 2), 1973, 147-152;

D. Sweeney: "A Correlation for Pressure Drop in Two-Phase Concurrent Flow in Packed Beds"; AIChE-Journal, Vol. 13, 7/1967, 663-669;

V. W. Weekman, J. E. Myers: "Fluid-Flow Characteristics of Concurrent Gas-Liquid Flow in Packed Beds"; AIChE-Journal, Vol 10 (No. 6), 11/1964,951-957;

R. P. Larkins, R. P. White, D. W. Jeffrey: "Two-Phase Concurrent Flow in Packed Beds"; AIChE-Journal, Vol 7 (No. 2), 6/1961, 231-239 or N. Midoux, M. Favier, J.- C. Charpentier: "Flow Pattern, Pressure Loss and Liquid Holdup Data in Gas-Liquid Down-Flow Packed Beds with Foaming and Nonfoaming Liquids"; J. Chem. Eng. Of Japan, Vol 9 (No. 5), 1976, 350-356.

Frequently, the relationship proposed by Midoux which has been tested for many gas-liquid systems is utilized. For example, in the case of nonfoaming systems:

$$\phi^2 = 1 + 1/X + 1.14/X^{0.54}$$

This relationship named after Lockart-Martinelli is illustrated graphically in many works; detailed discussions of it can be found in many process technology textbooks and publications, for instance also in Brauer et al.

The pressure drop of the biphasic flow $P_{gl}$ is then calculated from the experimentally determined or estimated, as detailed above, pressure drop of the pure flowing liquid phase $P_l$ using $$P_{gl} = \phi^2 * P_l$$

In the case of triphasic flow, as in the special case of the preparation of tertiary carboxylic acids by hydrocarboxylation of olefins, the calculation of the pressure drop becomes even more complex. In addition to the carbon monoxide phase and a liquid catalyst phase, the presence of an organic liquid phase has to be taken into account. This problem can be accounted for by the determination of a further dimesionless pressure $\phi^2_{org} = P_{gll}/P_{lg}$, so that the pressure drop can be determined as follows:

$$P_{gll} = \phi^2 * \phi^2_{org} * P_l$$

In general, with the reactor length L [m]

$$PD = P_{gl}/L \text{ or } PD = P_{gll}/L$$

The pressure drop of a multiphasic flow can thus be calculated by customary methods of chemical process technology. The same applies for the above-defined dimensionless pressure drop B, i.e. the loading factor of the multiphase reactor.

In one embodiment of the invention the size of the dimensionless loading factor B should be greater than or equal to 0.2, greater than or equal to 0.8, greater than or equal to 1 or greater than 3.

Higher cross-sectional loadings of the reactor (B>>1), recognizable by increasing pressure differential over the reactor, are possible at any time and even desired, as long the rising space-time yields may justify any increase in energy consumption. An upper limit is therefore given only by practical considerations such as energy consumption or difficulties in the separation of the phases on completion of reaction. From the process point of view, there is no fundamental upper limit, since the mixing of the phases rises with increasing superficial velocity. However, the risk of emulsion formation and thus of complications in phase separation outside the reactor also increase with increasing superficial velocity. In addition, the energy consumption increases with increasing superficial velocity (appropriately generated by a cycle stream of the catalyst solution). Thus, for technical and economic reasons, the loading factor is preferably not increased arbitrarily. The loading factor of one embodiment of the invention process may be less than 100, less than 50 or less than 30.

It is thus evident that, in addition to volume flow rates of the individual phases and the superficial velocities $w = V/(\pi D^2/4)$ derived therefrom, the apparatus dimensions of the reactor (Length L, diameter D) and also in particular the data of the random packings used (hydraulic diameter $d_H$, empty pipe fraction $\Psi$) play a role. The correct selection of these parameters may allow the process to be adapted without difficulty to highly differing requirements; in embodiments it may be required that, for example, $B \geq 0.2$, $B \geq 0.8$, $B \geq 1$, $B \geq 3$, or $B \geq 10$ or $B \geq 20$.

In the case of a slow reaction, it is possible, for example, to select a low hydraulic diameter of the random packing or a large specific surface area thereof, so that the required conditions for B are achieved even at small flow rates. In this way, sufficient residence times may be achieved via the length of a reactor having industrially viable dimensions. In the case of very fast reactions, the converse procedure may be used.

In other embodiments the ratio of the mass flow rate of the liquid phase $M_1$ comprising the catalyst to the mass flow rate of the disperse phase(s) M, may be greater than 1. In the case of hydrocarboxylation, the mass flow rate of the catalyst phase $M_1$ may be substantially greater than the mass flow rate of the disperse phases, i.e. of the organic olefin phase $M_{2a}$ and of the carbon monoxide-containing gas phase $M_{2b}$. In an embodiment of the invention, the mass ratio $M_1/M_2$ of the continuous phase ($M_1$) to the disperse phases ($M_2$) is greater than 2 or $M_1/M_2$ is >10. Flow ratios having $M_1/M_2 > 100$ are entirely possible and frequently even advantageous. The at least two reactants which are present dispersed in the continuous phase may be present as one phase (gas phase $M_{2a} + M_{2b} = M_{2(g)}$) dispersed in the continuous phase. This variant of the process according to the invention may always or sometimes be present when the reactants are both in the gaseous state under the reaction conditions. It is equally possible that the at least two reactants which are present dispersed in the continuous phase are present in two different disperse phases $M_{2a}$ and $M_{2b}$, which are each dispersed in the continuous phase. This variant of the process may be present when one of the reactants is present as a gas and one of the reactants as a liquid phase or in a liquid phase under the reaction conditions. In another embodiment this variant is always present when one of the reactants is present as a gas and one of the reactants as a liquid phase or in a liquid phase under the reaction conditions Under the condition $M_1/M_2 > 2$, the catalyst phase is the continuous phase, while the disperse phases are distributed in fine bubbles or in fine droplets. In an embodiment of the process according to the invention, it is possible that at least one reactant is dispersed by the energy introduced into the tubular reactor by the continuous phase. This leads to distribution of at least one reactant in bubbles or drops within the continuous catalyst phase.

Both bubble size and droplet size can be estimated by customary engineering methods. Suitable for this purpose are approaches using dimensionless parameters such as $$d_S/d_H = k * Re_{gl(gll)}^m * We_{gl(gll)}^n$$

where $d_S$ is the Sauter diameter of the drops or bubbles (in Brauer et al.)

$d_H$ is the hydraulic packing diameter, $Re_{gl(gll)}$ is the Reynolds number of the multiphasic flow $= w_{gl(gll)} * (\rho_1/\eta_1) * (d_H/\Psi)$, $We_{gl(gll)}$ is the Weber number of the multiphasic flow $= w_{gl(gll)}^2 * (\rho_1/\sigma_{gl}) * (d_H/\Psi^2)$, k, m, n are each empirical constants (known or to be determined experimentally), w are each superficial velocities $[m/s] = V/(\pi D^2/4)$, V is the volume flow rate under operation conditions $[m^3/s]$, $\rho$ is the density under operating conditions $[kg/m^3]$, $\eta$ is the viscosity under operating conditions $[Pa*s]$ and $\gamma$ is the interface tension under operating conditions $[N/m]$ and the indices l (liquid phase), g (gas phase), gl (gas/liquid biphasic flow) and gll (gas/liquid/liquid triphasic flow).

In the case of structured packings such as Sulzer SMV or narrow tubes as internals a calculated bubble or drop diameter ds greater than the channel diameter may not be viable. However, this may not apply to permeable structured packings and random packings, for example wire mesh rings or wire mesh fabrics (known as demister packings or drop separators). In an embodiment of the process according to the invention, calculated drop diameters may be used which are at least equal to or less than the hydraulic channel diameter:

$$d_S/d_H <= 1, \text{ and may be } <0.9.$$

From the calculated drop diameter, it is finally possible to calculate a mass transfer surface area according to $$A_S = 6\phi_l/d_S \; [m^2/m^3].$$

Quite analogously, for the mass transfer surface area of the gas bubbles:

$$A_S = 6\phi_g/d_S \; [m^2/m^3]$$

For the phase fraction $\phi_g$ of the disperse gaseous phase (in the case of hydrocarboxylation, the carbon monoxide-containing gas and the organic phase are dispersed), it is possible to insert $$\phi_g \sim w_g / \Sigma w_i$$

into the above equation. In this case, $\Sigma w_i$ is the sum of all three phases.

Quite correspondingly, for the phase fraction $\phi_l$ of the liquid phase:

$$\phi_l \sim w_l/\Sigma w_i$$

The residence time $\tau$ of the phases flowing through the reactor can be calculated approximately by $\tau \sim B^*_{\psi}/w_{gl}$. The residence time $\tau$ in the process according to the invention may be below one hour and may be in the range of minutes or even below. For example, the residence time $\tau$ may be 1 hour, 0.5 hour, 0.4 hour, 0.3 hour, 0.2 hour, 0.1 hour, 10 minutes, 5 minutes, 2 minutes and 0.5 minutes. Nevertheless, it is possible in this highly unusual method (high catalyst throughput in the reactor, comparatively very low fraction of reactants in the reaction mixture, resulting in turn in very short residence time) to achieve surprisingly high space-time yields in many multiphase reactions. Alternatively, at the same space-time yields, it is possible to work at distinctly lower temperatures than usual, since the increase in the reaction rate, which can result, for example, in the minimization of subsequent reactions and thus improve selectivity, permits it economically.

The invention process may be adapted very flexibly to highly differing demands. For specific demands, there are the following possible embodiments of the process according to the invention:

The reactor may be operated from top to bottom or from bottom to top or in another direction.

When the use requires a very long mixing zone or rest zones are required, for example, to withdraw streams, a battery arrangement of tubular reactors with internals or random packings may be selected.

A battery of tubular reactors or the alternative arrangement of packed and empty tube sections is possible and is to be recommended when a particularly low pressure drop is desired.

Moreover, the parallel arrangement of tubular reactors or the use of a multitube reactor, in which case the tubes can assume the function of the internals, may be used. In addition, reactors usable in the process according to the invention may be provided with multiple feeding of gas over the reactor length when the gas consumption is sufficiently high that unfavorable phase ratios of gas to liquid result in the combination of the two phases upstream of the reactor.

Some special conditions permit further embodiments of the invention process. For instance, high circulation of the catalyst phase or of the continuous phase may be additionally utilized for the operation (drive) of a jet nozzle which is disposed upstream of the actual tubular reactor as a liquid jet gas compressor. This may be used to thoroughly premix the two phases and to compress the gas phase, which enables operation at higher prepressures in the reactor. Finally, when, conversely, the suction action is utilized instead of the compression of the gas, it is possible to circulate gas with simultaneous premixing of the phases. The energy introduced into the tubular reactor with the continuous phase comprising the catalyst may thus be used to disperse the reactant phases or at least one reactant.

The supply of heat in the case of strongly exothermic reactions is uncritical in one or more embodiments of the invention process. The high throughput of the catalyst circulation may function as a heat carrier, so that even in the case of adiabatic operation of the reactor, only small temperature differences arise and a homogeneous temperature distribution in the reactor without temperature peaks results. The heat generated may conveniently be removed by a conventional heat exchanger arranged as desired in the external catalyst circuit or be utilized for energy generation. For better heat removal, it may be favorable under some circumstances to raise the catalyst circulation even higher (i.e. at a higher B value) than is necessary according to the experimental results, since the catalyst circuit can be used to set a small temperature gradient over the reactor.

In comparison to the prior art, embodiments of the invention process offer considerable advantages, including:

High space-time yields can be achieved at comparatively low temperatures.

The formation of by-products is extremely low; values of 1-2% by weight or even less are possible.

The catalyst is protected, the deactivation is very low and continuous discharge can thus be dispensed with.

In a particular embodiment of the invention process, at least one olefin is hydrocarboxylated in the multiphase reaction to give a carboxylic acid. In this embodiment of the invention process, the reactants include at least water, carbon monoxide and at least one olefin, the water being present as a reactant in the continuous phase, and the carbon monoxide and the at least one olefin dispersed in the continuous phase as droplets or bubbles for example. Carbon monoxide and at least one olefin may be present as a gaseous phase dispersed in the continuous phase. It is equally possible that carbon monoxide and at least one olefin are present in two different dispersed phases, i.e. as a gaseous phase and liquid phase.

In another embodiment of the invention process, carboxylic acids including tertiary carboxylic acids, may be prepared by hydrocarboxylating olefins, the catalyst phase may comprise a complex mixture of $BF_3$, HF, $H_2O$ and at least one metal ion, such as for example Cu ions. If the catalyst phase comprises a complex mixture and contains only copper as a metal, this complex mixture (this complex) may have the composition specified hereinbelow.

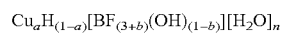

$$Cu_aH_{(1-a)}[BF_{(3+b)}(OH)_{(1-b)}][H_2O]_n$$

where
a=from 0.05 to 0.15
b=from 0 to 0.5 and
n=from 0.5 to 1.

The catalyst mixture may be prepared from commercial chemicals such as boron oxide, boron trifluoride, tetrafluoroboric acid, boron trifluoride dihydrate, hydrogen fluoride, copper or copper compounds and optionally water by mixing in appropriate stoichiometric ratios.

In addition, similar complex liquids in which copper is partly or fully replaced by one or more transition metal(s), for example silver, may be used as the catalyst liquid. The percentage water content A of the catalyst phase is calculated from the catalyst formula specified, as follows:

$$A=18*100*[(1-a)+n]/\text{total molar mass}$$

The reactants used for hydrocarboxylation may be one or more olefinic compounds (olefins) including one olefin or a mixture of a plurality of olefins having from 4 to 25 carbon atoms and/or having from 4 to 16 carbon atoms. The position of the double bond may be terminal or internal. The mixtures may consist of olefins of the same, similar (+2) or distinctly different (>+2) number of carbon atoms. Examples of olefins which may be present as reactants include: 1- or 2-pentene, 2-methylbutene, 1-, 2- or 3-hexene, 1-heptene, linear heptenes having internal double bond, mixtures of linear heptenes, 2- or 3-methyl-1-hexene, 1-octene, linear octenes having internal double bond, mixtures of linear octenes, 2, 3-methylheptene, 1-nonene, linear nonenes having internal double bond, mixtures of linear nonenes, 2-, 3- or 4-methyl-1-octene, 1-, 2-, 3-, 4- or 5-decene, 2-ethyl-1-octene, 1-dodecene, linear dodecenes having internal double bond, mixtures of linear dodecenes, 1-tetradecene, linear tetradecenes having internal double bond, mixtures of linear tetradecenes, 1-hexadecene, linear hexadecenes having internal double bond, mixtures of linear hexadecenes. Suitable reactants also include the isomeric hexene mixture obtained in the dimerization of propene (dipropene), the isomeric octene mixture obtained in the dimerization of butenes (dibutene), the isomeric nonene mixture obtained in the trimerization of propene (tripropene), the isomeric dodecene mixture obtrained in the tetramerization of propene or trimerization of butenes (tetrapropene or tributene), the hexadecene mixture obtained in the tetramerization of butenes (tetrabutene) and also olefin mixtures prepared by cooligomerization of olefins having varying carbon number (preferably from 2 to 4), optionally after distillative separation into fractions having the same or different (±2) carbon number. In addition, olefin or olefin mixtures which have been obtained by Fischer-Tropsch synthesis may be used. Furthermore, olefins which have been prepared by olefin metathesis or by other industrial processes may be used. Preferred reactants are isomeric octene, nonene, dodecene or hexadecene mixtures, especially those which have been obtained by oligomerization of lower olefins such as n-butenes or propene. The olefins may be $C_8$ olefins and/or isomeric mixtures of $C_8$ olefins. Other very suitable reactants are mixtures which consist substantially of isomeric $C_5$ olefins.

In addition, olefins having a methyl branch at one of the second carbon atoms (counted from both chain ends) and an iso index of 1, and also mixtures which comprise large fractions of such olefins, are valuable starting materials, since the hydrocarboxylation thereof may result in tertiary carboxylic acids having two alkyl groups in the 2-position.

The olefins may (under standard conditions) be gaseous, solid or liquid. When a gaseous olefin is used, the invention process may initially be a biphasic reaction, and a liquid product phase may form during the reaction. In other cases, there is already a triphasic system at the start of the reaction. Solid olefins are used as solutions. The solvents are inert liquids which are barely soluble in the catalyst phase, if at all. Solvents which have a distinctly different boiling point to the products to be prepared may be used since this eases distillative removal and recycling. Liquid olefins may also be used as solutions. The concentration of the olefin used and the sum of all olefins used in the solution may vary from 5% by mass up to above 99% by mass.

The second reactant in the process according to the invention is carbon monoxide. It is possible to use pure carbon monoxide or carbon monoxide-containing gas mixtures whose other gas constituents are inert under reaction conditions. Suitable gas mixtures are, for example, synthesis gas or other mixtures of carbon monoxide and hydrogen. Further inert gases in carbon monoxide mixtures may be, for example, nitrogen, methane, ethane or propane. The carbon monoxide content in these mixtures is generally not a critical parameter. However, gases having a carbon monoxide content below 10% by weight may cause the space-time yield to fall, and product and reactant could be lost with the offgas. The use of synthesis gas frequently offers a cost advantage. To achieve high selectivities pure carbon monoxide or gas mixtures which have from 85 to 99% by mass or 95 to 99% by mass, of carbon monoxide may be used.

Embodiments of the invention process may be carried out in such a way that the molar ratio of carbon monoxide to olefin (or sum of all olefins) at the entrance to the reactor is greater than 1. With increasing ratio of carbon monoxide to olefin, side reactions, for example the oligomerization of the starting olefin or of the starting olefins, are suppressed. A molar ratio between 2:1 and 5:1 may be employed.

The third reactant used is water. This is present in the catalyst phase in the mixture.

The specific residence time, the mass ratios of the phases and the loading factor can be selected within wide ranges. The adjustable parameters are dependent upon the number of tubular reactors, and also the presence and the dimensioning of any internals present.

In the hydrocarboxylation of olefins, for example in the hydrocarboxylation of $C_8$ olefins, a mass ratio of catalyst phase to olefin phase (olefin and any solvent present) at the reactor inlet in the range from 10/1 to 1000/1, in the range from 100/1 to 700/1, and/or in the range from 150/1 to 500/1, may be established.

The mass ratio of catalyst phase and carbon monoxide-containing feed gas (feed gas and any inert gas present) in the hydrocarboxylation, for example the hydrocarboxylation of $C_8$ olefins, maybe, for example, from 50:1 to 1000:1 and from 80:1 to 700:1.

The reactants may be fed preheated, i.e. with a temperature in the region of reaction temperature, or cold. Owing to the high phase ratio of catalyst phase to dispersed reactant phases, the preheating may also be effected by the process heat.

The hydrocarboxylating may proceed in a temperature range of from 10° C. to 150° C., and/or in the range from 20° C. to 60° C. The total pressure at which the process according to the invention may be carried out is from 0.1 to to 30 MPa, from 0.1 to 5 MPa, and/or from 0.5 to 2 MPa.

The flow through the tubular reactor may be in cocurrent from top to bottom or vice versa. For safety reasons, charging from above may be used. The tubular reactor can be operated in such a way that one or two of the phases present in the tubular reactor is fully or partly recycled.

The mixture leaving the reactor may be degassed, for example, in a gas-liquid separation vessel. The gas-liquid separation may be effected at the same pressure as at the reactor outlet. This is particularly advantageous when at least a portion of the gas removed (decompression gas) is to be recycled into the reactor. Otherwise, decompression may also be effected at lower pressure (down to 0.1 MPa).

The recycling of the offgas into the reactor may be carried out, for example, when it contains mainly carbon monoxide. This is the case, for example, when pure carbon monoxide is used as the reactant gas. When, for example, synthesis gas is used as the reactant gas, the offgas consists mainly of hydrogen. This may be utilized, for example, as heating gas or be worked up to pure hydrogen. The offgas, when it is not recycled into the tubular reactor, may be cooled before feeding to a workup or disposal, and condensate which arises is recycled into the process or fed to the workup of the entire reactor product or of the liquid constituents of the reactor product. Optionally, volatile carboxylic acids may be washed out of the offgas stream with water. The solution obtained in this case may be used, for example, as a wash solution for the crude product.

When the gas removed is fully or partly recycled, this may be achieved in a known manner, for example by a mixing nozzle which is mounted upstream of the reactor in the catalyst circulation stream, or by a cycle has compressor.

The degassed liquid mixture may be separated in a liquid-liquid separating vessel into the catalyst phase and a product phase. This separation may be effected in settling vessels of various design or centrifuges. For reasons of cost settling vessels may be used. Optionally, gas removal and separation of the two liquid phases may be carried out in the same apparatus.

The catalyst solution removed is fully or partly, preferably fully, recycled into the tubular reactor. The catalyst solution is supplemented by the amount of water consumed as a reactant in the reaction. The water used for supplementation may be fresh water or water which is obtained in the workup of the streams arising in the process according to the invention.

The product stream removed (crude carboxylic acid) may still contain small amounts of catalyst. In order to keep the catalyst losses small and to obtain a substantially catalyst-free product, it may be advantageous to extract the product stream with water. This may be effected appropriately in countercurrent in industrially customary apparatus. The extraction may be carried out at temperatures of from 0 to 200° C. In most cases, it is appropriate to carry out the extraction in the temperature range from 15 to 95° C. at atmospheric pressure.

The aqueous extract obtained in the scrubbing of the crude product may be introduced (pumped) into the catalyst phase recycled from the separating vessel to the reactor. Care has to be taken that only as much water is fed into the catalyst phase as is consumed in the hydrocarboxylation. When the extract contains more water than is needed to correct the water level several embodiments may be used. A first embodiment includes discharging a portion of the extracts. However, this may lead to catalyst losses. A second embodiment includes removing a portion of the water before the recycling, for example by distillation or by membrane separation. When the extract contains too little water, fresh water is additionally fed into the catalyst solution.

The washed crude product may be worked up to the predominantly tertiary carboxylic acids by known processes, for example by distillation.

The heat of reaction formed in the reaction may be removed via various heat exchangers. In this case, the heat exchangers do not have to be in the vicinity of the reaction chamber, but may also be anywhere outside the reactor. The individual heat flows are dependent upon the specific heat of reaction and also upon the desired temperatures in the reactor and in the workup apparatus. Type and size and also installation location of the heat exchangers used are dependent upon these parameters. The heat exchangers may be disposed especially in the recycling of the phases, especially of the continuous phase.

The carboxylic acids prepared in accordance with the invention may be used, for example, to prepare siccatives, peroxy esters or lubricants. In addition, they may be used to prepare unsaturated esters, for example for vinyl esters which find use as comonomers.

A block scheme of a plant in which the process according to the invention can be carried out is shown in FIG. 1, although the intention is not to restrict the process according to the invention to the embodiment illustrated there.

In FIG. 1, at the top of the hydrocarboxylation reactor 1, the catalyst phase 8 is fed in together with olefin 2, carbon monoxide-containing gas 3 and water 4. The mixture 5 obtained as a reaction mixture from the reactor 1 is separated in the settling vessel 6 into residual gas 7, catalyst phase 8 and product phase 9. The catalyst is, optionally after discharging a small portion and replacing it with fresh catalyst, recycled into the reactor 1 with the aid of a circulation pump. The residual gas 7 is cooled in the condenser 10 and any condensate obtained is passed into the vessel 6 through a line which is not shown. The product phase 9 removed is washed with water 13 in the vessel 12. The wash water 15 may partly replace the fresh water 4. The washed product phase 14 may be worked up by known processes.

The examples which follow are intended to illustrate the invention in detail without restricting the scope of the claims.

Experimental Setup:

The experiments were carried out in a continuous experimental apparatus whose setup corresponds substantially to the block scheme (FIG. 1).

In a reactor (bubble column or flow tube) (1), catalyst phase (8), olefin (2) (diluted with n heptane or cyclohexane) and synthesis gas (3) were reacted. From the reactor, the triphasic mixture went to the phase separator (6) (vessel with installed weir). The heavy liquid catalyst phase (8) settled and went back to the reactor (1) via a centrifugal pump. The lighter organic phase (9) ran over the weir into a second chamber of the phase separator and was drawn off under level control. The hydrogen which was present in the synthesis gas (3) and did not take part in the reaction, and also unconverted synthesis gas, degassed in (6) and were fed to an offgas scrubber G not shown in FIG. 1. There, volatile carboxylic acids and catalyst constituents were washed out with water. The wash water (13) obtained was used to wash the crude product (9) to free it of catalyst in the extractor (12) and the resulting extract was pumped into the catalyst phase.

The starting olefin used was an octene mixture prepared by the OCTOL process of OXENO Olefinchemie GmbH by oligomerization of n-butene or butene distillation cuts. In experiments 1 to 28, the octene mixture used (dibutene) had the following composition: 13% n-octenes, 62% 3-methylheptenes, 24% 3,4-dimethylhexenes, 1% other C8 olefins.

The CO source used was industrial synthesis gas having 50-55% by volume of CO (remainder hydrogen) or pure carbon monoxide.

The catalyst used was a complex of $BF_3$, HF, $H_2O$ and $Cu^+$ which satisfies the following formula:

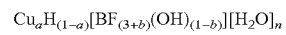

$$Cu_a H_{(1-a)}[BF_{(3+b)}(OH)_{(1-b)}][H_2O]_n$$

where a=from 0.05 to 0.15, b=from 0 to 0.5 and n=from 0.5 to 1.

Water consumed in the reaction was replaced by demineralized water.

EXAMPLE 1

Comparative Example

The reactor used was a bubble column. The catalyst phase was pumped in at the foot of the column. Dibutene and synthesis gas were fed in via separate frits likewise at the foot of the column. The top of the reactor was extended as a degasser for the residual gas; the liquid constituents ran over to a phase separator (settler).

Dimensions of the reactor:

| | |
|---|---|
| Length (liquid column up to overflow) | 4400 mm |
| Internal diameter | 209 mm |
| Volume of the liquid column approx. | 150 liters |

During the experiment, the catalyst composition varied within the following limits:

| | |
|---|---|
| a = from 0.09 to 0.10 mol/mol | (Cu⁺ based on boron) |
| b = from 0.1 to 0.2 mol/mol | (i.e. fluorine based on boron = from 3.1 to 3.2 mol/mol) |
| n = from 0.8 to 0.9 mol/mol | |
| Pressure (downstream of reactor) | 1.5 MPa gauge |
| Temperature (downstream of reactor) | from 30 to 35° C. |

The best results were achieved with the following data:

| | |
|---|---|
| Catalyst circulation | 2.0 t/h (about 1.2 m/h at 20° C.) |
| Synthesis gas | 10 m³/h under standard conditions (0° C., 0.1013 MPa) |
| Olefin input | 35 kg/h |

The conversion varied in the range from 50 to 60 mol %, the selectivity in the range from 78 to 81%. The remainder of the product stream consisted substantially of dimerized dibutene in addition to traces of longer- and shorter-chain acids, $C_8$ alcohols and esters of $C_8$ alcohols with the carboxylic acids formed. Over 99% of the carboxylic acids obtained had tertiary branching.

The total space-time yield of the nonanoic acids was from 0.14 to 0.15 t/(m³*h) (based on the liquid-filled part of the bubble column).

The calculated loading factor B when using a bubble column without random packing was in the range from $4*10^{-6}$ to $5*10^{-6}$.

EXAMPLES 2 to 11

In a reduced-scale laboratory apparatus according to the above-described principle, experiments were carried out in a cocurrent column having random packing. The reactor used was a DN 50 tube (internal diameter 53 mm) having a length of 1000 mm which was charged over a length of 950 mm with wire mesh rings (Vereinigte Füllkörper Fabriken, VFF; 4×4 mm with strut, calculated hydraulic diameter $d_H$=1.913 mm, free volume 91.5%). The reactor volume used was the empty pipe volume of the random packing layer, and was 2.10 liters. Catalyst, synthesis gas and organic reactant phase (olefin in cyclohexane, each 50% by mass) were combined directly upstream of the reactor without further mixing apparatus. The flow through the reactor was from top to bottom.

The synthesis gas was metered in at a controlled rate, the reactant mixture was introduced via a pump (determination of amount from the volume decrease of the reservoir) and the catalyst circulation was adjusted via a centrifugal pump. The catalyst concentration specified was the average of analyses at the start, during and after the experiments. Conversion and selectivity were determined by gas chromatography analysis of the crude product collected over 3 hours of constant operation.

The cross-sectional loading of the reactor was varied at 3 different catalyst phase/reactant phase ratios.

The results which follow show that there is only a slight change in the conversion and the selectivity at constant cross-sectional loading of the reactor despite falling residence time. Accordingly, the space-time yield increases in an almost linear manner with the cross-sectional loading at the same phase ratios. In experiment 5, a space-time yield of 0.272 t/m³/h was achieved at a selectivity of 95.2 mol % and an olefin conversion of 94.3%. In experiment 9, a space-time yield of 0.441 t/(m³*h) was achieved, a value about three times higher than with the bubble column in example 1.

TABLE 1

Experimental data of examples 2 to 11

| | Experiment | | | | | | | | | |
|---|---|---|---|---|---|---|---|---|---|---|
| | 2 | 3 | 4 | 5 | 6 | 7 | 8 | 9 | 10 | 11 |
| Pressure (MPa) | 1.5 | 1.5 | 1.5 | 1.5 | 1.5 | 1.5 | 1.5 | 1.5 | 1.5 | 1.5 |
| Temperature (° C.) | 31 | 31 | 32 | 33 | 34 | 32 | 35 | 34 | 32 | 31 |
| Catalyst (kg/h) | 44 | 98 | 146 | 195 | 49 | 98 | 146 | 195 | 49 | 98 |
| Catalyst (l/h) | 27 | 61 | 91 | 121 | 30 | 61 | 91 | 122 | 30 | 61 |
| Water/boron (mol/mol) | 1.73 | 1.74 | 1.8 | 1.7 | 1.78 | 1.78 | 1.87 | 1.77 | 1.78 | 1.99 |
| Fluorine/boron (mol/mol) | 3.1 | 2.92 | 3.19 | 2.91 | 3.16 | 3.16 | 3.24 | 2.88 | 3.16 | 3.31 |
| Cu+/boron (mol/mol) | 0.01 | 0.01 | 0.009 | 0.01 | 0.01 | 0.01 | 0.011 | 0.009 | 0.01 | 0.012 |
| Synthesis gas (kg/h) | 0.068 | 0.138 | 0.208 | 0.272 | 0.141 | 0.277 | 0.415 | 0.545 | 0.277 | 0.554 |
| Synthesis gas (l/h) | 7 | 14 | 21 | 28 | 14 | 28 | 42 | 56 | 28 | 56 |
| CO fraction (% by vol.) | 51 | 52 | 52 | 51 | 53 | 52 | 52 | 51 | 52 | 52 |
| Reactant (kg/h) | 0.22 | 0.45 | 0.71 | 0.90 | 0.47 | 0.82 | 1.38 | 1.73 | 0.89 | 1.76 |
| Reactant (l/h) | 0.3 | 0.62 | 0.98 | 1.25 | 0.65 | 1.14 | 1.91 | 2.40 | 1.24 | 2.43 |
| Olefin fraction (% by mass) | 50 | 50 | 50 | 50 | 50 | 50 | 50 | 50 | 50 | 50 |
| Residence time (s) | 218 | 100 | 67 | 50 | 168 | 84 | 56 | 42 | 127 | 64 |
| Mass ratio of catalyst to synthesis gas) | 644 | 704 | 704 | 716 | 346 | 352 | 352 | 358 | 176 | 176 |
| Mass ratio of catalyst to reactant) | 399.6 | 436.7 | 412 | 433.2 | 208.1 | 237.9 | 212.6 | 224.8 | 109.2 | 111 |
| Mass ratio of synthesis gas to reactant) | 0.62 | 0.62 | 0.59 | 0.60 | 0.60 | 0.60 | 0.60 | 0.63 | 0.62 | 0.63 |
| Conversion (%) | 99.6 | 88.5 | 93.7 | 94.3 | 82.6 | 89.0 | 90.2 | 83.9 | 77.3 | 42.7 |
| Selectivity (%) | 95.7 | 94.7 | 95.2 | 95.2 | 89.4 | 87.9 | 92.5 | 90.1 | 81.4 | 79.1 |
| STY (t/m³ * h) | 0.068 | 0.126 | 0.213 | 0.272 | 0.116 | 0.216 | 0.386 | 0.441 | 0.189 | 0.200 |
| Loading factor B | 0.043 | 0.097 | 0.148 | 0.201 | 0.060 | 0.124 | 0.186 | 0.260 | 0.089 | 0.187 |

EXAMPLES 12 to 16

In order to be able test higher cross-sectional loadings in the apparatus available, the reactor was scaled down by inserting a Teflon lining. The reactor then had an internal diameter of only 30 mm; the random packing layer was again 950 mm. The random packings used were again the 4×4 mm wire mesh rings as in examples 2 to 11.

Although the experiments showed a certain influence of the catalyst composition on selectivity and conversion, it could be clearly seen that the space-time yield had increased further. In experiment 16, an almost 10-fold increase was achieved at 1.375 t/(m³*h) compared to the comparative experiment in the bubble column (example 1)!

TABLE 2

Experimental data of examples 12 to 16

|  | Experiment | | | | |
| --- | --- | --- | --- | --- | --- |
|  | 12 | 13 | 14 | 15 | 16 |
| Pressure (MPa) | 1.5 | 1.5 | 1.5 | 1.5 | 1.5 |
| Temperature (° C.) | 31 | 35 | 37 | 42 | 43 |
| Catalyst (kg/h) | 137 | 187 | 172 | 171 | 171 |
| Catalyst (l/h) | 85 | 117 | 108 | 107 | 107 |
| Water/boron (mol/mol) | 1.96 | 2.08 | 2.05 | 1.92 | 1.81 |
| Fluorine/boron (mol/mol) | 3 | 3.18 | 3.20 | 3.24 | 3.34 |
| Cu+/boron (mol/mol) | 0.008 | 0.015 | 0.018 | 0.018 | 0.018 |
| Synthesis gas (kg/h) | 0.199 | 0.265 | 0.485 | 0.485 | 0.485 |
| Synthesis gas (l (STP)/h) | 200 | 270 | 500 | 500 | 500 |
| CO fraction (% by volume) | 52 | 52 | 52 | 52 | 52 |
| Reactant (kg/h) | 0.64 | 0.861 | 1.52 | 1.46 | 1.49 |
| Reactant (l/h) | 0.881 | 1.191 | 2.121 | 2.053 | 2.096 |
| Olefin fraction (% by mass) | 50 | 50 | 50 | 50 | 50 |
| Residence time (s) | 23 | 17 | 15 | 15 | 15 |
| Mass ratio of catalyst to synthesis gas) | 687 | 705 | 355 | 352 | 352 |
| Mass ratio of catalyst to reactant) | 428.7 | 436.4 | 226.3 | 233.1 | 228.5 |
| Mass ratio of synthesis gas to reactant) | 0.62 | 0.62 | 0.64 | 0.66 | 0.65 |
| Conversion (%) | 74.5 | 84.7 | 81.0 | 94.7 | 97.6 |
| Selectivity (%) | 88.0 | 88.1 | 86.3 | 92.9 | 89.8 |
| STY (t/m³ * h) | 0.439 | 0.671 | 1.118 | 1.353 | 1.375 |
| Loading factor B | 0.522 | 0.740 | 0.855 | 0.812 | 0.806 |

EXAMPLES 17 to 24

An even smaller reactor was installed into the experimental plant used in example 2: internal diameter 11 mm, length 900 mm (random packing zone).

The experimental results demonstrate that, despite the extremely short residence time, high conversions were still achieved; the space-time yields rose to almost 17 t/(m³*h). This was an increase by over two powers of ten compared to the reaction in the bubble column (example 1).

TABLE 3

Experimental data for examples 17 to 24

|  | Experiment | | | | | | | |
| --- | --- | --- | --- | --- | --- | --- | --- | --- |
|  | 17 | 18 | 19 | 20 | 21 | 22 | 23 | 24 |
| Pressure (MPa) | 0.8 | 0.8 | 0.8 | 1.5 | 1.5 | 1.5 | 1.5 | 1.5 |
| Temperature (° C.) | 31 | 34 | 32 | 30 | 30 | 31 | 34 | 40 |
| Catalyst (kg/h) | 73 | 146 | 219 | 146 | 146 | 239 | 81 | 229 |
| Catalyst (l/h) | 45 | 91 | 137 | 91 | 91 | 149 | 51 | 144 |
| Water/boron (mol/mol) | 1.88 | 2.13 | 2.09 | 2.01 | 1.91 | 1.75 | 1.92 | 1.95 |
| Fluorine/boron (mol/mol) | 3.44 | 3.64 | 3.66 | 3.45 | 3.37 | 3.1 | 3.53 | 3.50 |
| Cu+/boron (mol/mol) | 0.02 | 0.019 | 0.02 | 0.02 | 0.017 | 0.015 | 0.017 | 0.006 |
| (Synthesis gas) (kg/h) | 0.187 | 0.375 | 0.562 | 0.208 | 0.208 | 0.340 | 0.340 | 0.692 |
| (Synthesis gas) (l (STP)/h) | 19 | 37 | 56 | 21 | 21 | 35 | 35 | 72 |
| CO fraction (% by volume) | 100 | 100 | 100 | 52 | 52 | 51 | 51 | 52 |
| Reactant (kg/h) | 0.34 | 0.67 | 0.97 | 0.69 | 0.66 | 1.05 | 1.05 | 2.14 |
| Reactant (l/h) | 0.466 | 0.935 | 1.349 | 0.951 | 0.911 | 1.459 | 1.459 | 3.000 |
| Olefin fraction (% by mass) | 50 | 50 | 50 | 50 | 50 | 50 | 50 | 50 |
| Residence time (s) | 5 | 3 | 2 | 3 | 3 | 2 | 4 | 1 |
| Mass ratio of catalyst to synthesis gas) | 390 | 390 | 390 | 704 | 704 | 702 | 239 | 331 |
| Mass ratio of catalyst to reactant) | 434.4 | 434.4 | 450.7 | 425.1 | 444.0 | 453.3 | 155.3 | 213.7 |
| Mass ratio of synthesis gas to reactant) | 1.11 | 1.11 | 1.16 | 0.60 | 0.63 | 0.65 | 0.65 | 0.65 |
| Conversion (%) | 95.3 | 96.6 | 96.8 | 94.9 | 95.4 | 98.3 | 95.1 | 97.2 |
| Selectivity (%) | 86.9 | 93.0 | 89.9 | 89.8 | 88.9 | 91.1 | 85.4 | 93.3 |
| STY (t/m³ * h) | 2.30 | 4.989 | 6.987 | 4.836 | 4.608 | 7.784 | 7.011 | 16.040 |
| Loading factor B | 2.657 | 7.438 | 14.603 | 6.041 | 6.039 | 13.518 | 4.013 | 16.851 |

EXAMPLES 25 to 28

In this experimental series, operation was effected with pure carbon monoxide (>99%) and the influence of the CO pressure was investigated. In addition, manometers were installed in the reactor and permitted the measurement of the pressure differential over the reactor. In addition, temperature measurement sensors were installed in order to measure the temperature increase in the reactor. The reactor had a length of 1000 mm (random packing zone), an internal diameter of 16.0 mm and was fully insulated with Armaflex tubes against radiative heat loss so that approximately adiabatic operation was realized.

The measurements demonstrated that, at high space-time yield (from 10 to 11 t/($m^3$*h)) with pure carbon monoxide and increasing pressure, the selectivity can be improved. In experiment 28, virtually complete conversion and a selectivity of almost 97% was achieved. The temperature increase over the reactor at 2.8° C. was still sufficiently low that there were not heat removal problems. Nor was the pressure differential of 0.07 MPa a technical problem.

TABLE 4

Experimental data of examples 25 to 28

|  | Experiment | | | |
|---|---|---|---|---|
|  | 25 | 26 | 27 | 28 |
| Pressure (MPa) | 0.5 | 1.0 | 1.5 | 2.0 |
| Temperature (° C.) | 40 | 42 | 43 | 44 |
| Catalyst (kg/h) | 241 | 244 | 244 | 244 |
| Catalyst (l/h) | 151 | 153 | 153 | 153 |
| Water/boron (mol/mol) | 1.48 | 1.56 | 1.57 | 1.55 |
| Fluorine/boron (mol/mol) | 3.23 | 3.26 | 3.31 | 3.44 |
| Cu+/boron (mol/mol) | 0.007 | 0.007 | 0.007 | 0.007 |
| Synthesis gas (kg/h) | 0.999 | 0.999 | 0.999 | 0.999 |
| (Synthesis gas) (l (STP)/h) | 153 | 153 | 153 | 153 |
| CO fraction (% by volume) | 100 | 100 | 100 | 100 |
| Reactant (kg/h) | 2.93 | 2.93 | 2.93 | 2.93 |
| Reactant (l/h) | 4.095 | 4.105 | 4.110 | 4.115 |
| Olefin fraction (% by mass) | 50 | 50 | 50 | 50 |
| Residence time (s) | 2 | 3 | 3 | 4 |
| Mass ratio of catalyst to synthesis gas) | 241 | 244 | 244 | 244 |
| Mass ratio of catalyst to reactant) | 164.3 | 166.5 | 166.5 | 166.5 |
| Mass ratio of synthesis gas to reactant) | 0.68 | 0.68 | 0.68 | 0.68 |
| Conversion (%) | 99.6 | 99.6 | 99.6 | 99.6 |
| Selectivity (%) | 92.2 | 95.3 | 96.2 | 96.8 |
| STY (t/$m^3$ * h) | 9.432 | 9.749 | 9.832 | 9.903 |
| Loading factor B | 12.595 | 8.833 | 7.420 | 6.677 |

EXAMPLES 29-30

The plant used in examples 2 to 28 was used to carry out the process according to the invention using another reaction dimension and other random packings.

The reactor used was a DN 40 tube (internal diameter 44.3 mm) of length 2000 mm, flowed through from top to bottom. The tube was charged to a length of 1920 mm with Sulzer SMV 8 mixers. The empty pipe volume based on the random packing length was 2.96 liters.

The reactant used was an olefin mixture of substantially internally branched olefins which, according to gas chromatography analysis, had the following composition:

| 2,4-Dimethylhexene | 2.54% by volume |
|---|---|
| 3,3-Dimethylhexene | 1.02% by volume |
| 2,3-Dimethylhexene | 1.60% by volume |
| 3,4-Dimethylhexene | 63.54% by volume |
| 3-Methylheptene | 29.13% by volume |
| Other octenes | 2.14% by volume |

The olefin mixture was mixed with n-heptane at the start of the experiment and initially charged in a vessel. After phase separation with the water required for the reaction was washed to free it of catalyst; the washing waters went back to the reactor. The washed crude product went to a distillation column in which the solvent and unconverted olefin were removed overhead. Solvent and residual olefin were recycled to the reservoir vessel for the feed mixture. Consumed olefin was replaced by feeding into the reservoir vessel under level control.

The plant was operated continuously, and only small amounts of solvent occasionally had to be replaced which had been lost in the distillation as a result of inadequate condensation. It was possible to prepare a mixture of tertiary nonanoic acids having a purity of 99.8% and in a selectivity of from 93 to 96%.

TABLE 5

Experimental data of examples 29 and 30

|  | Experiment | |
|---|---|---|
|  | 29 | 30 |
| Pressure (MPa) | 1.5 | 1.5 |
| Temperature (° C.) | 22 | 27 |
| Catalyst (kg/h) | 5.999 | 5.999 |
| Catalyst (l/h) | 3.643 | 3.659 |
| Water/boron (mol/mol) | 1.49 | 1.53 |
| Fluorine/boron (mol/mol) | 3.36 | 3.33 |
| Cu+/boron (mol/mol) | 0.0127 | 0.0136 |
| Synthesis gas (kg/h) | 10.313 | 9.669 |
| Synthesis gas (l (STP)/h) | 1001 | 934 |
| CO fraction (% by volume) | 52.3 | 53.6 |
| Reactant (kg/h) | 49.04 | 43.92 |
| Reactant (l/h) | 67.16 | 60.49 |
| Olefin fraction (% by mass) | 40 | 55 |
| Residence time (s) | 2 | 2 |
| Mass ratio of catalyst to synthesis gas) | 582 | 620 |
| Mass ratio of catalyst to reactant) | 305.8 | 248.4 |
| Mass ratio of synthesis gas to reactant) | 0.53 | 0.40 |
| Conversion (%) | 99.2 | 97.5 |
| Selectivity (%) | 94.3 | 96.9 |
| STY (t/$m^3$ * h) | 8.747 | 10.766 |
| Loading factor B | 3.606 | 3.511 |

German application 102004011081.6 filed on Mar. 6, 2004 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A process for hydrocarboxylating at least one olefin to form a carboxylic acid comprising:
   carrying out a continuous flow multiphase reaction catalytically to produce a carboxylic acid in a tubular reactor;
   wherein the continuous flow multiphase reaction comprises:
   a continuous phase; and at least one disperse phase;
wherein water and a catalyst are present in the continuous phase,
the carbon monoxide and the at least one olefin are present as one or more phases dispersed in the continuous phase,
the catalyst comprises $BF_3$, HF, $H_2O$ and at least one transition metal ion, and
a loading factor, B, of the tubular reactor is greater than or equal to 0.2.

2. The process of claim 1, wherein the carbon monoxide and at least one olefin are present in the continuous phase in two different dispersed phases.

3. The process of claim 1, wherein the loading factor is greater than or equal to 0.9.

4. The process of claim 1, wherein the loading factor is greater than or equal to 1.0.

5. The process of claim 1, wherein a mass ratio of the continuous phase to a total dispersed phase is greater than 2.

6. The process of claim 1, further comprising:
driving a jet nozzle located upstream of the tubular reactor with the continuous phase.

7. The process of claim 1, further comprising:
dispersing the carbon monoxide and/or the at least one olefin by the energy introduced into the tubular reactor by the continuous phase.

8. The process of claim 1, wherein the at least one olefin has from 4 to 25 carbon atoms.

9. The process of claim 1, wherein carbon monoxide and at least one olefin are dispersed in the continuous phase as a gaseous phase.

10. The process of claim 1, wherein carbon monoxide and at least one olefin are present in two different dispersed phases.

11. The process of claim 1, wherein the catalyst comprises a complex of the formula $$Cu_a H_{(1-a)}[BF_{(3+b)}(OH)_{(1-b)}][H_2O]_n$$

where a=from 0.05 to 0.15,
b=from 0.00 to 0.50 and
n=from 0.50 to 1.00.

12. The process of claim 1, wherein the multiphase reaction of water, carbon monoxide and at least one olefin is carried out at a temperature of from 10 to 150° C.

13. The process of claim 1, wherein a molar ratio of carbon monoxide to olefin is from 2:1 to 5:1.

14. The process of claim 1, wherein a mass ratio of continuous phase to at least one olefin dispersed in the continuous phase is from 10:1 to 1000:1.

15. The process of claim 1, wherein a mass ratio of continuous phase to carbon monoxide dispersed in the continuous phase is from 50:1 to 1000:1.

16. The process of claim 1, wherein the at least one olefin is at least one selected from the group consisting of $C_8$ olefins.

* * * * *